United States Patent [19]

Borysko

[11] Patent Number: 4,777,096

[45] Date of Patent: Oct. 11, 1988

[54] SHEET CONTAINING A PLURALITY OF SURGICAL NEEDLES

[75] Inventor: Emil Borysko, Bridgewater, N.J.

[73] Assignee: Ethicon, Inc., Somerville, N.J.

[21] Appl. No.: 26,929

[22] Filed: Mar. 17, 1987

Related U.S. Application Data

[60] Continuation of Ser. No. 816,531, Jan. 6, 1986, abandoned, which is a division of Ser. No. 682,046, Dec. 14, 1984, Pat. No. 4,587,202.

[51] Int. Cl.$^4$ .............................................. A61B 17/06
[52] U.S. Cl. .................................... 428/571; 128/339; 428/577; 163/5
[58] Field of Search ............. 128/339; 223/102; 163/1, 5; 29/413, 415; 428/571, 577

[56] References Cited

U.S. PATENT DOCUMENTS 2,326,022  8/1943  Everett .............................. 113/112
2,479,464  8/1949  Bliss .................................. 128/339
3,054,172  9/1962  Turney ............................... 29/413
3,822,461  7/1974  Malmstrom ......................... 29/415

Primary Examiner—Michael H. Thaler
Attorney, Agent, or Firm—Charles J. Metz

[57] ABSTRACT

Surgical needles are produced by a process which comprises the steps of:

(a) coating at least one side of a metal sheet with a light sensitive photoresist;

(b) exposing the photoresist with light in the image of a plurality of surgical needles, each needle having a pointed end and a suture attachment end;

(c) removing the unexposed photoresist, to thereby leave in place on the metal sheet hardened photoresist in the image of a plurality of surgical needles;

(d) exposing the product of step (c) to an etchant to remove metal not protected by said hardened photoresist, to thereby form a plurality of surgical needles.

2 Claims, 5 Drawing Sheets

4,777,096

SHEET CONTAINING A PLURALITY OF SURGICAL NEEDLES

This is a continuation of application Ser. No. 816,531, filed Jan. 6, 1986, abandoned, which is a division of application Ser. No. 682,046, filed Dec. 14, 1984, now U.S. Pat. No. 4,587,202.

The invention relates to a photoetching process for making surgical needles that has particular applicability to the simultaneous manufacture of large numbers of surgical needles, to a sheet made by said process containing a plurality of surgical needles, and to certain surgical needles that can be made by said process.

BACKGROUND OF THE INVENTION

Surgical needles are made, one at a time, by a multi-step process involving considerable time, labor, and precision machinery. A brief outline of a typical process for making surgical needles is the following:

Stainless steel wire of the appropriate diameter is strightened and cut to the desired length to form a blank. One end of the blank is die-formed and/or ground to produce a cutting edge or point. The other end is either drilled to form a hollow receptacle for a surgical suture, or it is stamped to form a channel for swaging the suture. The point is sharpened, and the needle is bent As a rule, the final steps are a heat treatment to temper the needle, that is, to increase the hardness without imparting brittleness, and a polishing process. After this, sutures are attached to the needles by any of several means. On additional feature of the prior art process for making surgical needles is that the shape of the needle is limited by what can be done to a piece of wire. As will be apparent below, this invention provides a process that can be used to make any shape that can be drawn in two dimensions.

This multi-step process is acceptable for the production of relatively large surgical needles but with the advent of microsurgery and the need for ever smaller surgical needles, the process has proven to be quite inefficient for the production of small needles having diameters of, e.g., from one to three mils because of the large amount of skilled labor and precision machinery required in handling such small needles individually throughout the various steps of the process leading to attachment of sutures and final inspection.

This invention provides a process that is particularly well adapted to the efficient simultaneous production of large numbers of small size surgical needles.

BRIEF SUMMARY OF THE INVENTION

The process of the invention comprises the steps of:
(a) coating at least one side of a metal sheet with a light sensitive photoresist;
(b) exposing the photoresist with light in the image of a plurality of surgical needles (the dimensions of the image are modified to compensate for lateral etching during the etching step, as will be explained below);
(c) removing the unexposed photoresist, to thereby leave in place on the metal sheet hardened photoresist in the image of a plurality of surgical needles;
(d) exposing the product of step (c) to an etchant to remove metal not protected by said hardened photoresist, to thereby form a plurality of surgical needles.

The invention also provides a metal sheet containing a plurality of surgical needles.

THE PRIOR ART

Heath, in U.S. Pat. No. 2,735,763, discloses a photo-etching process for making small parts from a sheet of thin metal which will not withstand any mechanical working.

Jacks et al., in U.S. Pat. No. 3,358,363, discloses a photoetching process for making fuse elements.

Snyder, in U.S. Pat. No. 3,816,273, discloses a photo-etching process for making wire.

Poler, in U.S. Pat. No. 4,080,709, discloses a photo-etching process for making the mounting structure for an intra-ocular lens.

Dinardo, in U.S. Pat. No. 4,282,311, and James, in U.S. Pat. No. 4,284,712, disclose a photoetching process for making flyleads for video disc styli.

DETAILED DESCRIPTION OF THE INVENTION

Figure 1:
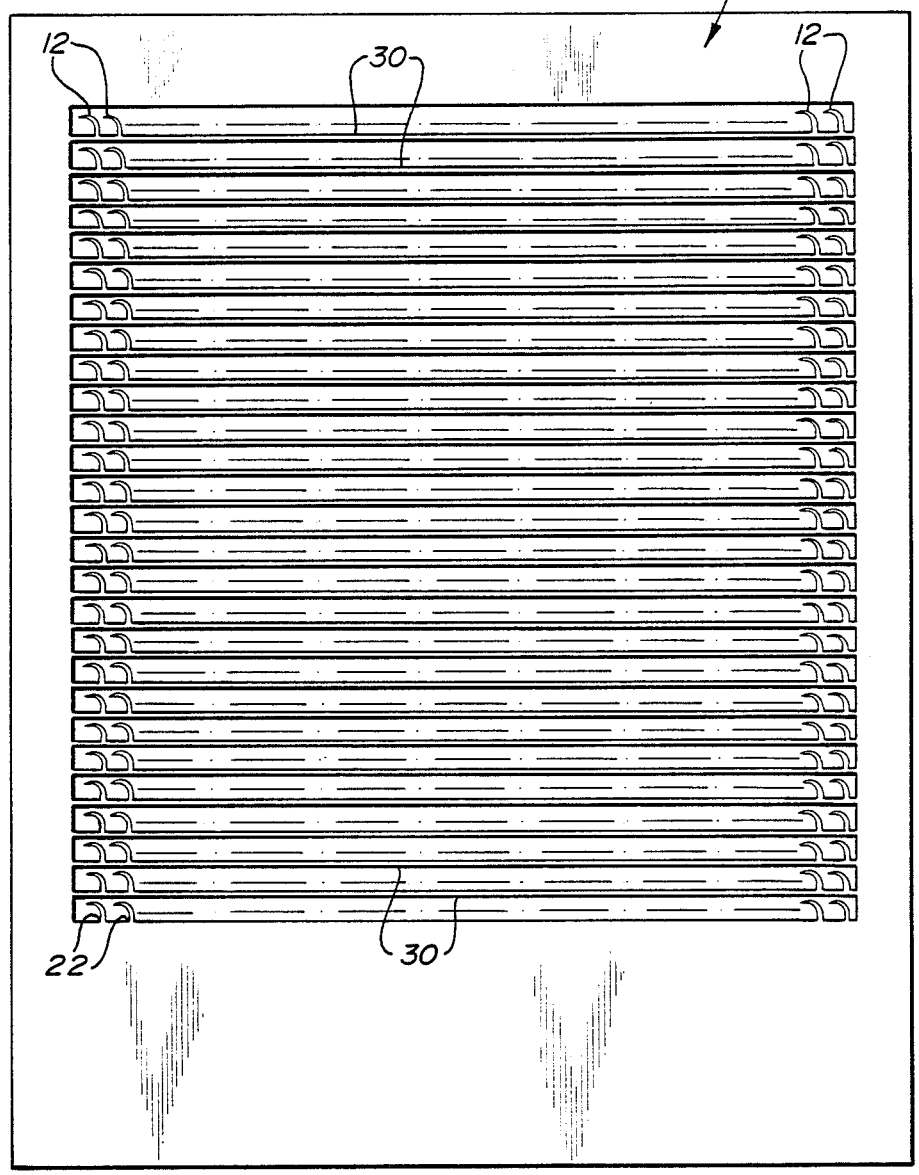
FIG. 1 is a top plane view of a metal sheet containing a plurality of surgical needles produced by the process of the invention.

The first step in the process of the invention is to coat at least one side of a metal sheet with a light sensitive photoresist material. The metal that is used can be selected so as to possess all of the strength, hardness, toughness, and grain structure, in the sheet form that the metal will need in the form of a surgical needle. This is one advantage over the current multi-step process for producing surgical needles, in which one step is usually a heat treatment step to develop optimum properties. Any metal or alloy that can be obtained in thin sheet form can be used, provided that it has the requisite properties of strength, hardness, etc. For instance, a tensile strength of at least about 300,000 psi, a Rockwell C hardness of at least 45, and ductility so that the needle can be bent up to about 90° and then straightened without breaking, are desirable. The metals that can be used include stainless steel, specifically, 320 stainless steel and Gin 5 and Gin 6 razor blade grade stainless steel, and molybdenum. Gin 6 stainless steel is preferred. The metal sheet will usually have a thickness of from about one to about ten mils.

The photoresist compositions used are known in the art. For instance, they are discussed in "Photo-Resist Materials and Processes" by William DeForest, McGraw-Hill 1975, and a wide variety of photoresist compositions are available commercially. The metal sheet can be coated with the photoresist by any convenient method, such as dip coating, spraying, and the like. In a preferred aspect of the invention, both sides of the sheet are coated with the photoresist and the needle images are formed on both sides. (In any event, the second side must be coated with either a photoresist or a protective coating.) In a typical coating process, the metal sheet is thoroughly cleaned, rinsed, dipped in dilute aqueous acid, e.g., 10% HCl, rinsed again, dried, and then coated. Since the photoresist compositions are sensitive to light, the coating should be carried out under "safe light" conditions, e.g., under yellow or orange light, or in the dark. After coating, the coated metal sheet is baked at a moderately elevated temperature for a few minutes, e.g., at about 80° C. for about 10 minutes, to dry the coating. After the coated sheet has cooled, it is then exposed to light in the image of a plurality of surgical needles, shaped to compensate for lateral etching of metal during the etching step, a principle that is well understood in the art. This is done by first covering the coated sheet with a negative or first photomask containing an image of the needles. An illustrative enlarged negative or first photomask of a single surgical needle is shown as 14 in FIG. 5 (it will be discussed in more detail) below. In a preferred aspect of the invention, the coated reverse side of the metal sheet is then covered with a second photomask that is the mirror image of the first photomask 14 and in perfect register therewith, and then exposed to light. An illustrative enlarged second photomask of a single surgical needle is shown as 16 in FIG. 6. As will be explained in more detail below, the said second photomask 16 may differ in certain details from the said first photomask 14. The light source used to expose the photoresist is rich in ultraviolet radiation. A carbon-arc light is preferred, but mercury-vapor lamps or ultraviolet rich fluorescent lights may also be used. Typical exposure times are within the range of a few seconds to several minutes, depending upon the nature and power of the light source, the distance of the light from the photoresist, and the sensitivity of the photoresist. The instructions of the manufacturer of the photoresist should be followed in this respect.

After exposure, the photoresist is rinsed in a suitable commercially available "developer" formulated for the particular photoresist being used, to remove the unexposed photoresist. After rinsing, the sheet with the photoresist coating in the form of surgical needles may be baked at, e.g., 120° to 260° C. for 5 to 10 minutes to further harden the remaining photoresist coating. The next step is to etch away the unwanted metal in an etching solution. Typical etching solutions include 36- to 42- degres Baumé aqueous ferric chloride, an aqueous mixture of ferric chloride and HCl, or a mixture of aqueous hydrocholoric acid and nitric acid, or the like. Such etching solutions are known in the art, as is their use in a photoetching process. After the etching step, there remains the desired surgical needles, which are removed from the etching solution, washed, and dried. The developed and hardened photoresist is then removed by dissolving away with a suitable commercially available stripper formulated for the photoresist being used. A detailed discussion of the application of the above process to a specific surgical needle design follows.

Figure 3:
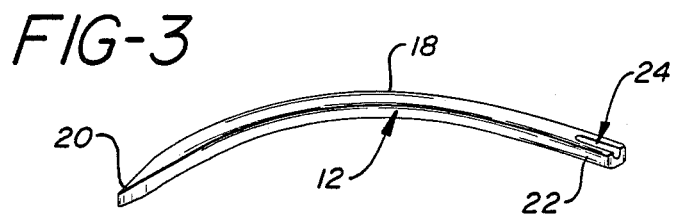
FIG. 3 is an enlarged perspective view of a surgical needle made by the process of the invention.
Figure 4:
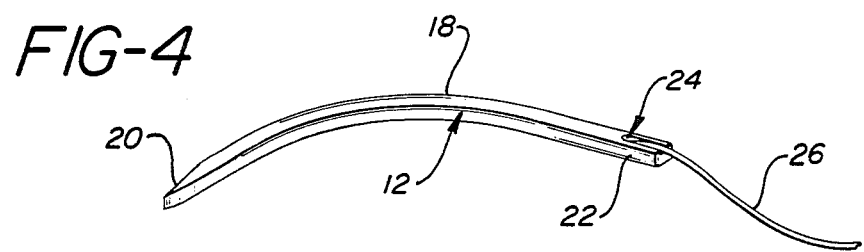
FIG. 4 is a perspective view of the needle of FIG. 3 attached to a surgical suture.

A surgical needle to be produced by the process of the invention is shown as 12 in FIG. 3. The needle includes a shank 18, a point 20, and a suture attachment end 22. In this design, the suture attachment end 22 includes a channel 24 by which a suture 26 may be attached, as is explained in more detail below. The first step in using the process of the invention to produce this needle 12 is to make a precision black drawing of the needle 12 several hundred times larger than the required finished size. This drawing is then optically reduced to the required size, and an exposure is made near the corner of a sheet of high resolution film. The film is moved laterally by a precision stepping device and a second exposure is made. This is repeated until a row of exposures across the film is completed. The stepping device moves the film upward by one row's width, and a second row of exposures is made. This process is repeated until the entire film area is covered. The film is then developed to produce a negative or photomask of the images of the needles.

Figure 2:
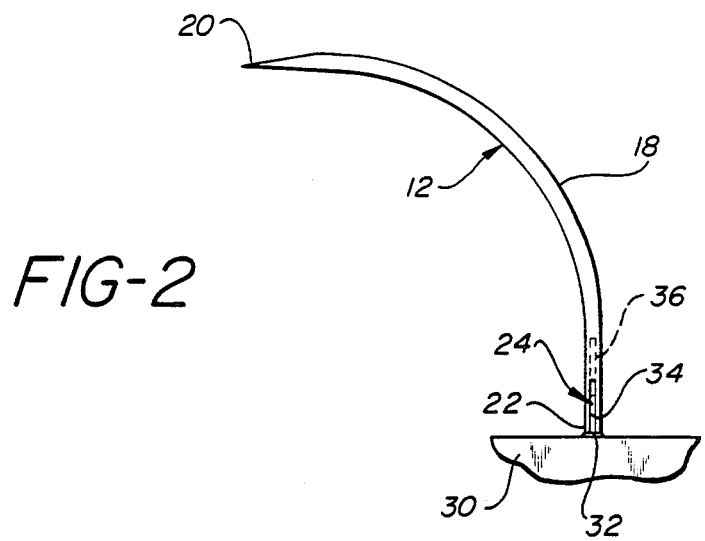
FIG. 2 is an enlargement of a portion of the sheet of FIG. 1.
Figure 5:
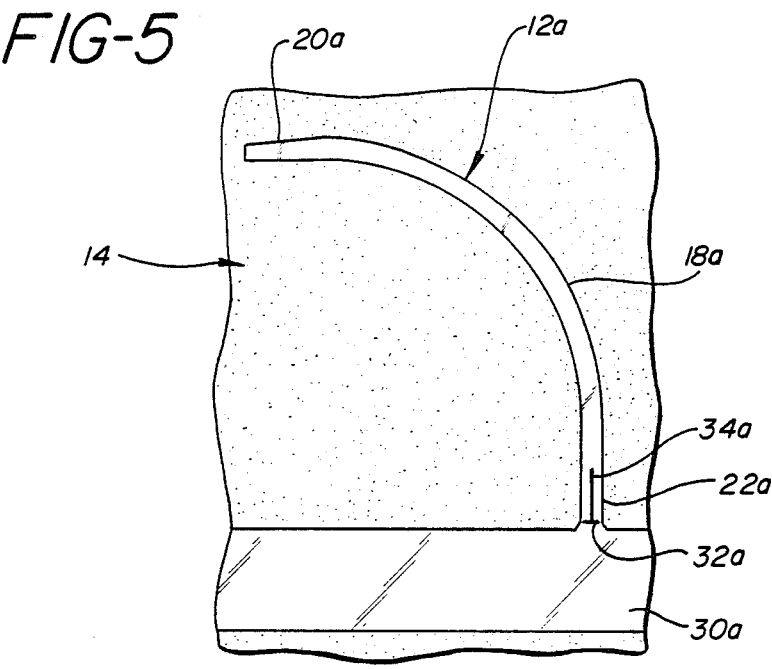
FIG. 5 is an enlarged plan view of a photomask of the image of a single surgical needle that can be used in carrying out the process of the invention.

FIG. 1 shows a sheet 28 containing a plurality of surgical needles 12 attached at their suture attachment ends 22 to continuous base rows 30 that extend the width of the sheet 28. An enlargement of a portion of the sheet 28 showing one needle 12 is shown in FIG. 2. An enlargement of a photomask 14 corresponding to this needle 12 is shown in FIG. 5. The dimensions of the image 12a of the needle in the photomask are modified to allow for lateral etching of the metal during the etching step. The photomask image of a particular part will be referred to by the same reference number, with the addition of an "a" to the number. Thus, the photomask image of the needle 12 is referred to by the reference number 12a.

Figure 7:
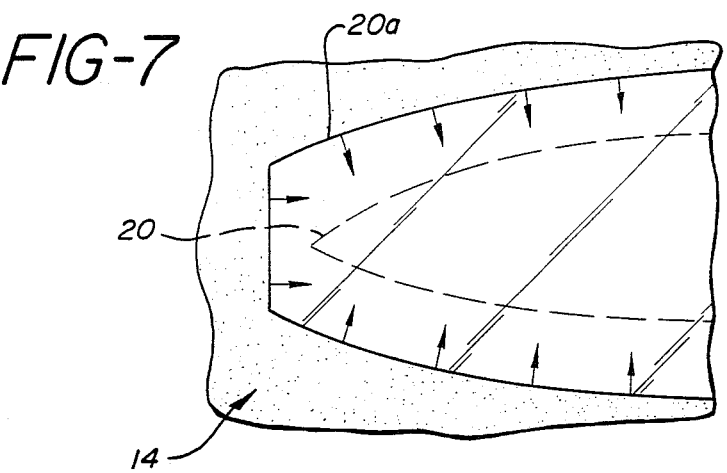
FIG. 7 is an enlarged view of a portion of FIG. 5.
Figure 8:
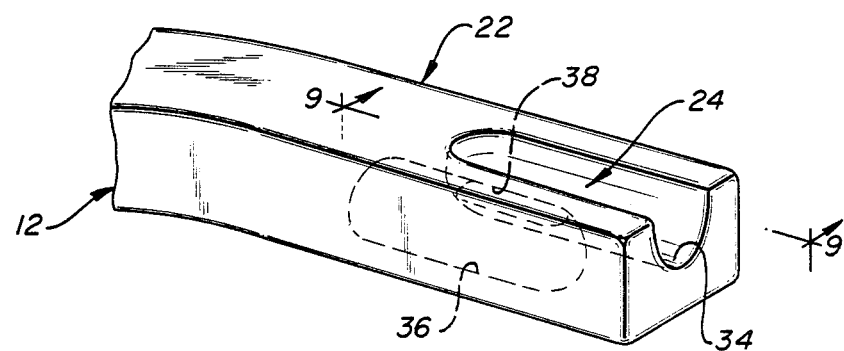
FIG. 8 is an enlarged perspective view of the suture attachment end of the needle of FIG. 3.

As a first approximation, the metal will be etched laterally about the same distance as vertically. Thus, in the preferred situation wherein the metal sheet is etched from both sides, lateral undercutting equal to approximately one-half the thickness of the sheet should be allowed for in the photomask. The image 20a of the needle's point in the photomask preferably does not come to a point, but rather is preferably blunted as is shown in FIG. 5. Lateral etching will cause a point to be formed. This is shown schematically in FIG. 7, which is an enlargement of the image 20a of the needle's point. The arrows show the direction of lateral etching of the metal so that, after the etching step, the point of the needle will have the configuration shown in dashed lines in FIG. 7. (If the needle's point were pointed in the photomask, after etching, the point would probably be rounded rather than sharply pointed, as a result of the lateral etching.)

Figure 10:
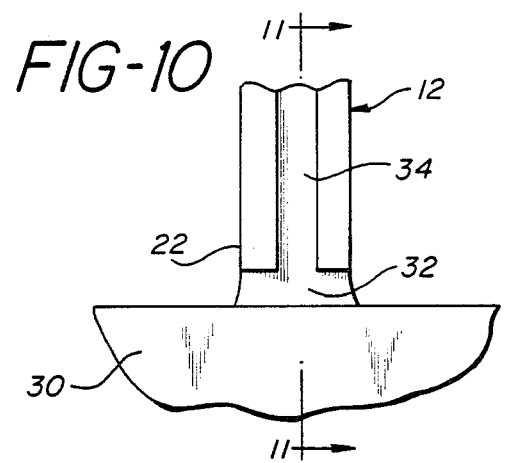
FIG. 10 is an enlarged view of a portion of FIG. 2.
Figure 11:
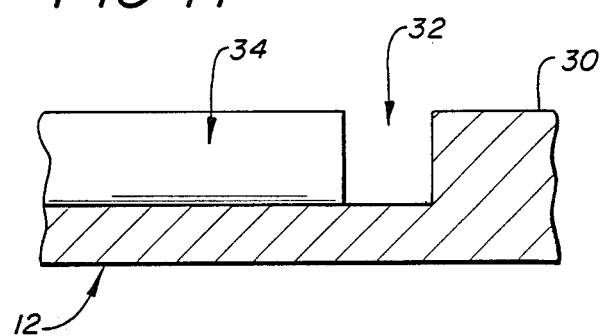
FIG. 11 is a cross-sectional elevation taken along line 11—11 of FIG. 10.
Figure 12:
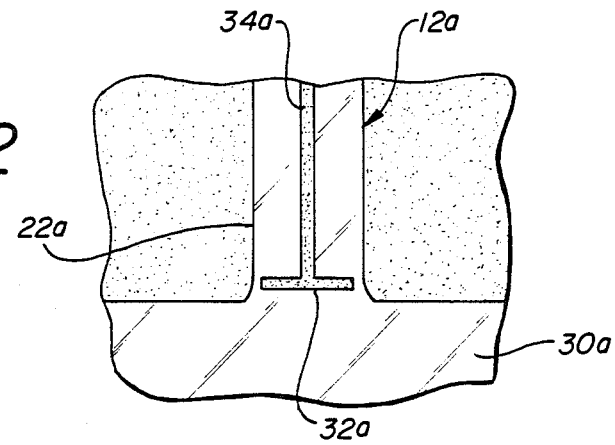
FIG. 12 is an enlargement of a portion of FIG. 5.

For ease of handling the needles produced by the process of the invention, it is preferred to produce the needles such that they are attached by a breakable connection to the metal sheet from which they are etched. By so doing, the needles can be kept separated and in order until they are ready for further processing. One way to do this is illustrated in the drawings (see, especially, FIGS. 1, 2, 5, and 6). The sheet 28 shown in FIG. 1 has the needles 12 attached to base rows 30 that extend all the way across the sheet. To assist in the removal of the individual needles 12 from the base rows 30, a transverse groove 32 may be made at the point of attachment of the needle 12 to the base row 30. (See FIGS. 10, 11 and 12.) In the photomask 14, the groove 32 is provided for by a transverse line 32a, in one of the two photomasks only, at the point of attachment to the base row 30a.

Figure 6:
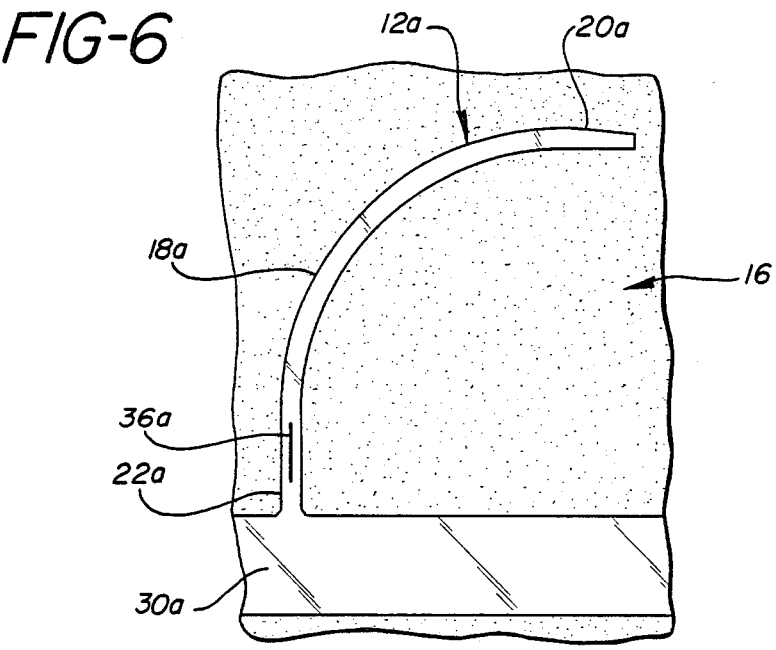
FIG. 6 is an enlarged plan view of a second photomask of the image of a single surgical needle that can be used in carrying out the process of the invention.
Figure 9:
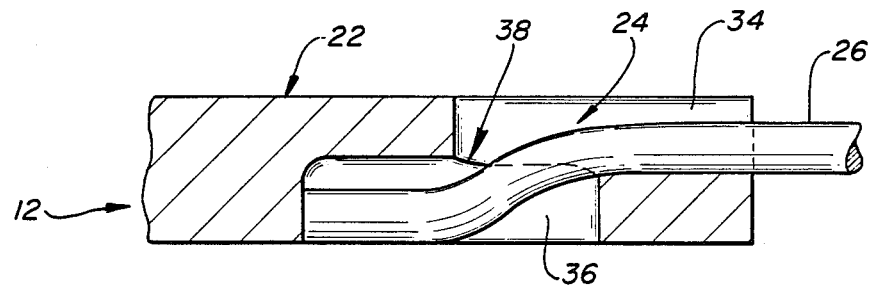
FIG. 9 is a cross-sectional view taken along line 9—9 of FIG. 8, and additionally showing a suture attached to the needle.

Referring now to FIGS. 5, 6, 8, and 9, the suture attachment end 22 includes a channel 24 for use in attaching the needle to a suture 26. In the embodiment shown, the channel 24 is a bilevel channel in which the first half 34 of the channel is offset longitudinally from the second half 36, as is shown clearly in FIGS. 8 and 9. The two halves of the channel are etched equally from both sides of the metal sheet so that each has a depth of about one half the thickness of the sheet. Where the two halves 34, 36 overlap, a hole 38 is produced so that the two halves 34, 36 communicate with each other. A suture 26 is attached by filling both halves 34, 36 with an adhesive material (not shown) such as an epoxy glue while the second half 36 is lying on a flat surface, and then inserting the end of a suture 26 through the hole 38 between the two halves, 34, 36 as is shown in FIG. 9. The epoxy resin is hardened at room temperature, and then given a final cure in an oven at moderately elevated temperatures, such as 40° to 60° C. The photomask images 34a, 36a, of the two halves of the channel are thin lines, as is shown in FIGS. 5 and 6, to allow for the lateral etching that will occur during the etching process. The "bilevel" channel decribed here has several advantageous properties. First, it serves to hold the suture securely in place while the adhesive sets, and, second, it helps to prevent the suture from being pulled out of the channel by a lateral force.

The needles 12 may be detached from the sheet 28 before attaching to a suture 26. This can be done by grasping a single needle 12 with forceps and flexing it at the breakoff groove 32. Alternatively, all needles in a single row can be detached simultaneously by cutting both ends of the base row 30, removing it from the sheet 28, and then pressing the row of needles lightly on to an adhesive surface. Flexing the base row 30 upwards will cause it to break off at the break-off grooves 32, leaving the needles precisley spaced and securely held on the adhesive surface in an ideal position for suture attachment.

After the etching step and after removal of the hardened photosist, if desired, entire sheets of needles may be electropolished using conventional electropolishing methods to smooth off rough edges, polish the surfaces, and improve the shape of the needle points by reducing or eliminating undesirable projections, and by sharpening the edge. This is another advantage of the invention, since hundreds, and perhaps thousands, of needles can be electropolished simultaneously in a few minutes.

A typical electropolishing bath is an aqueous sulfuric, phosphoric, and glycolic acid bath. Polishing times of about 30 seconds at ten volts and 90° C. are typical.

The invention has been described and claimed in terms of a dry positive photoresist technique, that is, the hardened photoresist on the metal sheet is in the image of the part that is to be made. It is theoretically possible to use a wet photoresist or a negative photoresist technique in carrying out the process of the invention, although to do so would be awkward and uneconomical.

What is claimed is:

1. A unitary metal sheet formed from a single sheet of metal containing a plurality of surgical needles, each needle having a pointed end and a suture attachment end, wherein the needles are arranged in a spaced relationship along a plurality of continuous rows, and wherein said needles are attached at said suture attachment end by breakable connections to base rows that extend substantially across the width of said sheet.

2. The metal sheet of claim 1 wherein the suture attachment end of said needle includes a bilevel channel including a channel on opposite sides of said needle, wherein the said two channels are offset longitudinally but overlap, and wherein the two channels communicate with each other at the overlap.

* * * * *